(12) United States Patent
Dietz

(10) Patent No.: US 11,221,202 B2
(45) Date of Patent: Jan. 11, 2022

(54) MULTIBEND SENSOR

(71) Applicant: Tactual Labs Co., New York, NY (US)

(72) Inventor: Paul Henry Dietz, Redmond, WA (US)

(73) Assignee: Tactual Labs Co., New York, NY (US)

( * ) Notice: Subject to any disclaimer, the term of this patent is extended or adjusted under 35 U.S.C. 154(b) by 209 days.

(21) Appl. No.: 16/270,805

(22) Filed: Feb. 8, 2019

(65) Prior Publication Data
US 2020/0124397 A1    Apr. 23, 2020

Related U.S. Application Data

(60) Provisional application No. 62/748,984, filed on Oct. 22, 2018.

(51) Int. Cl.
| | | |
|---|---|---|
| *G01B 7/28* | (2006.01) | |
| *G01D 5/241* | (2006.01) | |
| *G01D 5/26* | (2006.01) | |
| *G01D 5/16* | (2006.01) | |

(52) U.S. Cl.
CPC .............. *G01B 7/28* (2013.01); *G01D 5/241* (2013.01); *G01D 5/268* (2013.01); *G01D 5/16* (2013.01)

(58) Field of Classification Search
CPC ... G01B 7/28; G01B 7/20; G01B 7/24; G01D 5/268; G01D 5/241; G01D 5/16; G01D 3/08; A61B 5/1071; A61B 5/6826; A61B 2562/043; A61B 2562/164; G06F 3/014
See application file for complete search history.

(56) References Cited

U.S. PATENT DOCUMENTS

| | | | | |
|---|---|---|---|---|
| 8,931,351 B2* | 1/2015 | Muramatsu | ............... | G01D 5/16 73/849 |
| 2009/0293631 A1* | 12/2009 | Radivojevic | ............ | G06F 3/014 73/774 |
| 2010/0233421 A1* | 9/2010 | Lind | ..................... | E04B 1/3211 428/108 |
| 2012/0244398 A1* | 9/2012 | Youngs | ................. | B60L 3/0084 429/61 |
| 2016/0100244 A1* | 4/2016 | Gentile | ................ | H04R 1/1041 345/174 |
| 2016/0253031 A1* | 9/2016 | Cotton | .................. | G06F 3/0416 345/174 |
| 2016/0254328 A1* | 9/2016 | Song | .................... | H01L 27/3225 324/699 |
| 2017/0265810 A1* | 9/2017 | Van De Vyver | ..... | A61B 5/1121 |
| 2020/0378741 A1* | 12/2020 | Dietz | ..................... | G01B 11/16 |

* cited by examiner

*Primary Examiner* — Christopher P McAndrew
*Assistant Examiner* — Zannatul Ferdous
(74) *Attorney, Agent, or Firm* — Adam Landa

(57) ABSTRACT

A multibend sensor is able to provide information regarding bending of the sensor data in a manner able to mitigate error propagation. A reference strip and a sliding strip are separated from each other by a spacer. Electrodes are located on the reference strip and the sliding strip. The bending of the multibend sensor will be reflected in the shifting of the sliding strip with respect to the reference strip and the measurements obtained from the electrodes.

20 Claims, 14 Drawing Sheets

MULTIBEND SENSOR

This application claims the benefit of U.S. Provisional Application No. 62/748,984 filed Oct. 22, 2018, the contents of which are incorporated herein by reference. This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The disclosed apparatus and methods relate to the field of sensing, and in particular to providing accurate determination of positioning using a sensor.

BACKGROUND

In the past, sensing gloves have been employed to detect hand gestures. An example is the Dataglove, set forth in U.S. Pat. No. 5,097,252, which employed optical bend sensors along the fingers to detect finger position. Nintendo's Power Glove used a similar design, but with resistive bend sensors. In both cases, the bend sensors were not very sensitive, providing only a single measure of the overall bend for each bend sensor.

Bend sensors are used in applications beyond finger and hand sensing. They are often employed to understand human motion more generally. Additionally, bend sensors are used in robotics, sensing deformation in structures and space suit monitoring.

To better understand position of systems with multiple joints, some systems have used a bend sensor per joint, or at each point of articulation. There are challenges with this approach that limit its practicality. For example, the bend sensors have to be custom fitted for the spacing between joints. The need for fitting for the spacing can be problematic for tracking human motion because of size variation in people.

Additionally, there is the problem of cascaded error from the joint measurements. For example, the angle of each successive segment of a finger may be determined as the sum of the joint angles to that segment. Thus, any errors in the angle measurements taken for each of the preceding joints accumulate. This is why robot arms use extremely high precision angular encoders to find a modestly precise position. Unfortunately, inexpensive bend sensors have poor angular precision making them inadequate for understanding the impacts of cascaded joint error.

Systems have attempted to overcome this shortcoming by using cameras and other sensing techniques to directly measure finger positions. Camera-based techniques are challenged by the difficulty of finding good viewpoints from which to view what is happening. Other position sensor systems can be bulky and/or expensive. Inertial tracking can be used but it has severe drift issues.

Additionally there are Fiber Bragg Grating sensors that permit measuring bends along the length of a fiber bundle and can recover detailed shapes of a particular geometry. These sensors are difficult to make and require significant, bulky instrumentation and complex calibration. Further, they are expensive and impractical for most applications.

Therefore, there is a need for an improved method and apparatus for accurately determining bending through the use of sensors.

BRIEF DESCRIPTION OF THE DRAWINGS

The foregoing and other objects, features, and advantages of the disclosure will be apparent from the following more particular description of embodiments as illustrated in the accompanying drawings, in which reference characters refer to the same parts throughout the various views. The drawings are not necessarily to scale, emphasis instead being placed upon illustrating principles of the disclosed embodiments.

DETAILED DESCRIPTION

Figure 1:
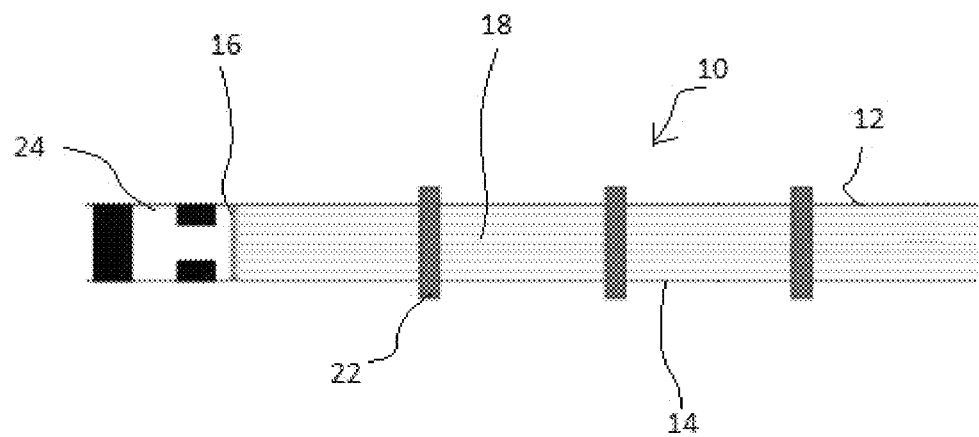
FIG. 1 shows a top down view of a sensor strip.

The present application describes various embodiments of sensors that are designed for accurately determining the bending of a sensor. The multibend sensor detects multiple bends along the length of the sensor and uses measurements taken to create an accurate determination of its current shape. In an embodiment, the multibend sensor comprises two flat, flexible strips. As used herein and throughout the application "strip" means a piece of material that is generally longer in one dimension than it is wide. A strip may be rectangular shaped, cylindrical shaped, or generally have an amorphous shape, provided one dimension is longer than the other. One of the strips is a reference strip and the other strip is a sliding strip. While the strips are referred to as reference strips and sliding strips it should be understood that the roles of reference strip and sliding strip are interchangeable. The reference strip and the sliding strip are separated by a spacer and mechanically joined on one end. The lengths of the reference strip and the sliding strip are substantially the same. A plurality of retainers can ensure that the strips remain pressed against the spacer so that the distance between the strips remains substantially constant when being used. At measurement points along the reference strip, that can be determined by a variety of different methods, the corresponding location on the sliding strip can be measured. When the multibend sensor is straight, the strips line up.

For example, a measurement point on a reference strip that is 1 cm from the attached end will align with a corresponding point on the sliding strip that is also at 1 cm when the strips are not bent. But if the multibend sensor is bent into a circular arc, or other bent shape, the strips will slide relative to each other. The inner strip in the arc will be along a smaller radius than the outer strip. Even though the strips are the same length, they will cover a different angular extant. With the strip conjoined on one end, the tighter the arc, the more the other ends will slide relative to each other, moving the free ends of the strips further apart. The multibend sensor works by measuring these relative shifts at many points along the sensor using capacitive electrodes or another suitable measuring method. By using the data acquired by the measuring method during the bending event, it is possible to determine the shape of the multibend sensor. This is true even in the case of multiple bends along the multibend sensor.

Unlike previous systems that measured angles independently at multiple points, by measuring the relative shift, it can be shown that measurement errors at one point do not impact the understanding of the angles at other points. This makes the multibend sensor less sensitive to measurement error. By measuring at many points the relative shift between flexible strips as they are bent into a complex fashion, the shape of the multibend sensor can be determined. Unlike the previous systems that measured angles independently at multiple points thereby accumulating error, by measuring shift, measurement errors at one point do not impact the understanding of absolute angle at other points. This makes the present invention less sensitive to measurement errors.

Figure 2:
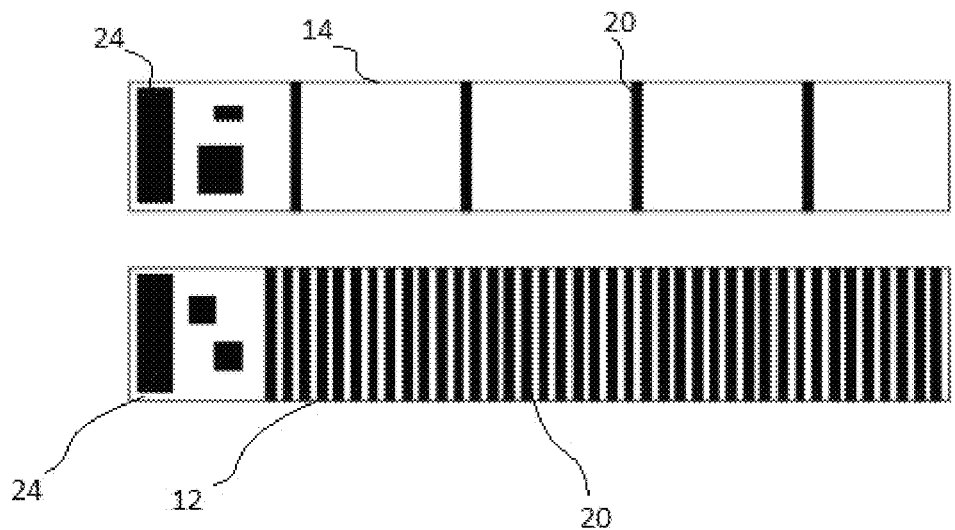
FIG. 2 shows a bottom up view of a sensor strip.

Referring now to FIGS. 1 and 2, shown is an embodiment of a multibend sensor 10. FIG. 1 shows a schematic side view of the multibend sensor 10. FIG. 2 shows a top and a bottom view of the multibend sensor 10. In the embodiment shown, the multibend sensor 10 has a sliding strip 12 and a reference strip 14. The sliding strip 12 is secured to the reference strip 14 at a distal end 16 of the reference strip 14. In the embodiment shown there is a spacer 18 located between the sliding strip 12 and the reference strip 18. Additionally shown are retainers 22 that retain the sliding strip 12 and the reference strip 14 against the spacer 18.

Operably connected to the sliding strip 12 and the reference strip 14 is circuitry 24 that is adapted to receive and process measurements that occur. In the embodiment shown, the circuitry 24 may comprise components, or be operably connected to components, such as processors, signal generators, receivers, etc.

The sliding strip 12 and the reference strip 14 may be formed from flexible printed circuit board strips. While the sliding strip 12 and the reference strip 14 are shown having specific electrode patterns, it should be understood that the roles of each of the respective strip may be changed and that the sliding strip 12 may function as the reference strip 14 and vice versa depending on the particular implementation. Electrodes 20 may be placed on the surfaces of the sliding strip 12 and the reference strip 14. The electrodes 20 are adapted to transmit and receive signals. The electrodes 20 may be arranged in any pattern that is capable of determining a change during the bending of the sliding strips 12 and the reference strip 14. Additionally, the number, size and shape of the electrodes 20 implemented on sliding strip 12 and the reference strip 14 may be changed based on a particular implementation.

Still referring to FIGS. 1 and 2, the sliding strip 12 and the reference strip 14 are flexible and able to move and bend. Additionally the spacer 18, which is placed between the sliding strip 12 and the reference strip 14, is flexible and able to move and bend. In an embodiment, the spacer 18 may have different levels of flexibility with respect to the sliding strip 12 and the reference strip 14. In an embodiment, the sliding strip 12, the reference strip 14 and the spacer 18 may each have different levels of flexibility. In an embodiment, there is no spacer 18 and the sliding strip 12 and the reference strip 14 move with respect to each other.

The spacer 18 used in the embodiments preferably keeps the strips spaced at a constant distance regardless of the amount of bending, yet still permits relative sliding. Spacer 18 preferably has a thickness that is able to permit there to be difference between the lengths of the sliding strip 12 and the reference strip 14 when there is bending. In an embodiment, there may be no spacer and the sliding strip 12 and the reference strip 14 may be abutting each other, however there should still be sufficient distance between the outward facing sides to permits sensing of the relative shift between the sliding strip 12 and the sliding strip 14 during a bend. In an embodiment, the spacer 18 may have the same flexibility as the sliding strip 12 and the reference strip 14. A thick spacer 18 will provide a good amount of shift, but the spacer 18 itself may change thickness with a tight bend. A thin spacer 18 will have this issue less but may not provide adequate shifting. In an embodiment, the spacer 18 may be made out of a series of thin layers which slide against each other. This allows a thick spacer 18 to have fairly tight bends without changing overall thickness.

Having a known spacing between the reference layer and sliding layers is assists in obtaining accurate data. Ensuring the spacing can be accomplished by different methods. As discussed above with respect to FIG. 1, retainers 22 can be affixed to one strip and provide compressive force to the other strip that slides against it as shown. The retainers 22 may be plastic or elastic pieces that provide a compressive force to the reference strip 14 and the sliding strip 12. The compressive force should be such that it maintains the distance but does not inhibit movement of the reference strip 14 and the sliding strip 12. In an embodiment, elastomeric sleeves can be used to achieve the same task, providing compressive force.

At the end portion 16, the sliding strip 12 and the reference strip 14 are secured together. In an embodiment, the sliding strip 12 and the reference strip 14 are mechanically attached together. In an embodiment, the sliding strip 12 and the reference strip 14 are integrally secured to each together. In an embodiment, the sliding strip 12 and the reference strip 14 are secured at a location other than the distal end. In an embodiment, the sliding strip 12 and the reference strip 14 are secured in the middle of the stip. Elsewhere along the lengths of the sliding strip 12 and the reference strip 14, the sliding strip 12 and the reference strip 14 slide with respect to each other. The sliding strip 12 and the reference strip 14 also slide against the spacer 18 relative to each other. The retainers 22 ensure that the sliding strip 12 and the reference strip 14 remain pressed against the spacer 18 so as to keep a constant distance between them. Circuitry 24 and electrical connections between the strips are outside of the sensing area where the bending occurs. In the embodiment shown in FIGS. 1 and 2, the circuitry 24 is located proximate to end portion 16 where the sliding strip 12 and the reference strip 14 are joined. The sliding strip 12 and the reference strips 14 contain patterns of electrodes 20 that will allow the electronics to detect the relative shift between the two strips at many locations by measuring the coupling from electrodes 20 on the sliding strip 12 and the electrodes 20 on the reference strip 14 through the spacer 18.

The embodiment discussed above may be made using the materials and techniques implemented to create flexible circuits. Flexible circuits may start with a flexible, insulating substrate such as polyimide. A thin conducting layer (such as copper, silver, gold, carbon, or some other suitably conducting material) is adhered to the substrate with an adhesive. In an embodiment, the conducting layer is patterned using photolithographic techniques. In an embodiment, the conducting layer is applied by sputtering. In an embodiment, the conducting layer is applied by printing. When applied via printing, conductive ink can be directly patterned onto the substrate.

Similar to rigid printed circuit boards (PCBs), flexible circuits can be manufactured to include multiple conductive layers, separated by insulators. Vias may provide connections among the different layers. Like rigid PCBs, standard electrical components may be affixed to flexible circuits using soldering and other well-known techniques. However, because some components are not flexible, flexing their attachments may lead to broken electrical connections. For this reason, flexible circuits may employ stiffeners in the area of components, so that that the region of the circuit does not appreciably flex. For similar reasons, flexible circuits tend not to place vias in regions that are actually bending since the stresses in those areas may sometimes lead to breakage.

Many electrode patterns for the multibend sensor can benefit from the use of interlayer connections in bending regions. Dupont® has developed special conductive inks that are explicitly designed to withstand repeated flexure. However other suitable flexible conductive inks may be used as well. These inks can be implemented in the multibend sensors discussed herein. Flexible inks permit flexible connections between conductive layers, serving the role of vias. It should be noted that these flexible conductive inks are compatible with a wide range of substrates, including fabric. This allows for the construction of multibend sensors that are directly integrated into clothing. Additionally, in an embodiment clothing is made from fibers that function as multibend sensors. When implementing multibend sensor fibers stiffeners may be added in order to restrict the movement of the multibend sensor fibers.

Figure 3:
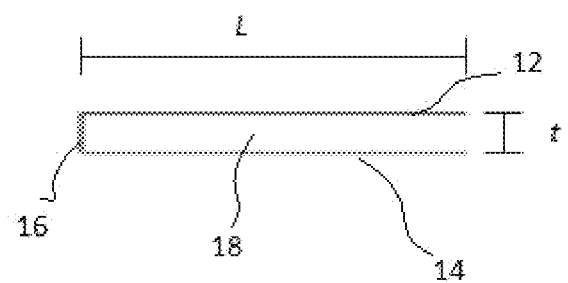
FIG. 3 is a schematic view of sliding and reference sensor strip.
Figure 4:
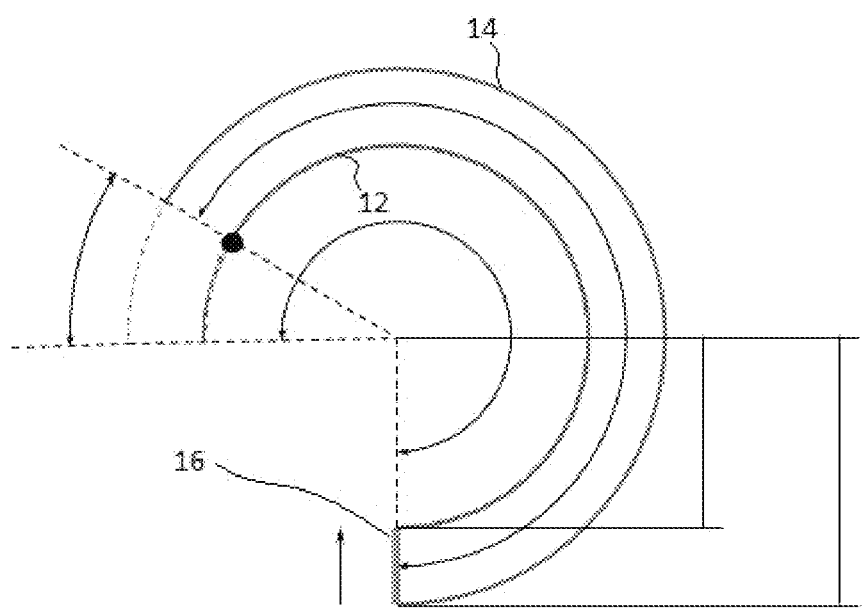
FIG. 4 is diagram illustrating a reference strip wrapped around a spacer.
Figure 5:
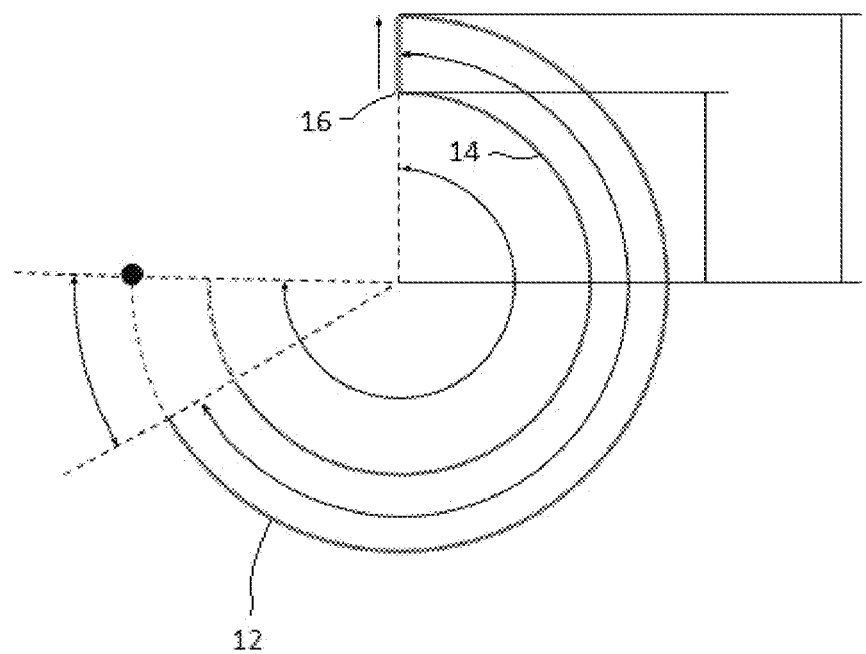
FIG. 5 is another diagram of a reference strip wrapped around a spacer.

Referring now to FIGS. 3-5, when the multibend sensor is wrapped around an object in a circle, the inner of the two strips conforms to the circle, while the outer strip conforms to a slightly larger circle due to the thickness of the spacer 18. Because the two strips have different radii of curvature, the unconstrained ends will not align with each other. By knowing the length of the strips, sliding strip 12 and reference strip 14 and the thickness of the spacer 18, the radii can directly be calculated. If the relative shift between the two strips at many places is measured a model of the bend as a series of circular arcs can be constructed. This provides a much better understanding of the shape of the bend as opposed to traditional sensors.

Still referring to FIGS. 3-5, to illustrate the way in which the multibend sensor works, take two strips of length L, the sliding strip 12 and the reference strip 14 separated by a spacer 18 of thickness t. The sliding strip 12 and the reference strip 14 are joined together at one end and cannot move relative to one another at that end. When the reference strip 14 is wrapped into a circle of radius r as shown in FIG. 4, the reference strip 14 will have a radius of curvature of r, while the sliding strip 12 will have a smaller radius of r−t.

The circumference of the circle is $2\pi r$. The reference strip 14, which is of length L, covers a fraction of the circle:

$$\frac{L}{2\pi r}$$

To put it in terms of radians, angle subtended by this strip is:

$$\theta_r = \frac{L}{r}$$

As shown in the diagram, when curled in the direction of the thickness measurement t, the sliding strip 12 ends up on the inside, with a smaller radius of curvature. The tighter wrap means that some of the sliding strip 12 extends beyond the end of the reference strip 14. If this continues along a circle of the same radius, the sliding strip 12 subtends an angle of:

$$\theta_s = \frac{L}{r-t}$$

The end of the reference strip 14 lines up with a corresponding point on the inner sliding strip 12. To give a more precise definition, it is the intersection point on the sliding strip 12 to the normal constructed through the endpoint of the reference strip 14.

This point can be found on the sliding strip 12 by finding the difference in the angular extent of the two arcs, finding the extending length $s_s$ and subtracting this from the total length L.

$$\theta_s - \theta_r = \frac{L}{(r-t)} - \frac{L}{r} = \frac{Lt}{r(r-t)}$$

The length of the segment $s_s$ of the sliding strip 12 that extends past the sliding strip 12 can be found by dividing the angular extent in radians by $2\pi$ to find the fraction of the circle and multiplying by the circumference.

$$s_s = \frac{Lt}{r(r-t)} \frac{1}{2\pi} 2\pi(r-t) = L\frac{t}{r}$$

Solving these equations for the radius r gives:

$$r = t\frac{L}{s_s}$$

By measuring the relative shift between the strips, the radius of curvature across the length can be calculated using this simple equation.

Now consider the case where bending occurs in a clockwise direction as shown in FIG. 5.

The analysis proceeds much as before, but now the sliding strip is on the outside, with a radius of curvature of r+t.

$$\theta_r = \frac{L}{r}$$

$$\theta_s = \frac{L}{r+t}$$

As before, the goal is to locate the point on the sliding strip 12 that corresponds to the endpoint of the reference strip 14. However, because the sliding strip 12 is on the outside and thus subtends a smaller angle the arc has to be continued to find the intersecting point. $s_s$ is calculated by finding the angle subtended and the corresponding length on the sliding strip.

$$\theta_r - \theta_s = \frac{L}{r} - \frac{L}{(r+t)} = \frac{Lt}{r(r+t)}$$

$$s_s = \frac{Lt}{r(r+t)} \frac{1}{2\pi} 2\pi(r+t) = L\frac{t}{r}$$

This is the same result as obtained in the counterclockwise case. The difference here is that $s_s$ in the first case is the amount the sliding strip 12 extended past the reference strip 14, and in this case, it is the amount extra that would be needed to reach the end of the reference strip 14.

To combine these two cases, consider the radius of curvature to be a signed quantity, with a positive r indicating an arc which proceeds in a counterclockwise direction and a negative r indicating a clockwise direction.

A new variable, $L_s$ is defined as the total length along the sliding strip 12 to line up with the end of the reference strip 14. The signed radius of curvature is:

$$r = t\frac{L}{L-L_s}$$

In FIG. 4, $L_s$<L, gave a positive radius of curvature. In FIG. 5, $L_s$>L, gives a negative radius of curvature. The signed radius of curvature is then used to find the signed angular extent of the reference strip.

$$\theta_r = \frac{L}{r} = \frac{L-L_s}{t}$$

In the following, all angles and radii of curvature are signed.

Reconstructing the Curve from Shift Measurements

In an embodiment, the multibend sensor models shape as a series of circular arcs of different radii to allow for complex curves. By measuring the relative shift at many points along the strips, the curvature of each segment can be quickly determined.

Figure 6:
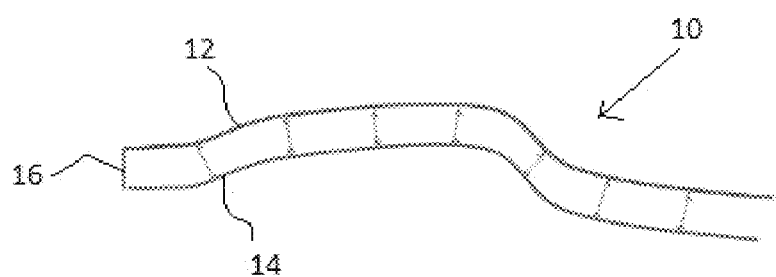
FIG. 6 is another view of a sensor strip formed from a sliding strip and a reference strip.

The multibend sensor 10 shown in FIG. 6 comprises a sliding strip 12 and a reference strip 14. Finding the shape of the reference strip 14 is the goal. At fixed intervals along the reference strip the corresponding shifted position along the sliding strip 12 is measured. By corresponding, it is meant that points that lie at the same angle with respect to the common center of the radius of curvature are used. Another way to say this is that if a normal to the curve of the reference strip 14 is constructed at the measurement point, a measurement will be made where it intersects the sliding strip 12.

$L_r[n]$ is the length of the reference strip 14 to measurement point n. $L_s[n]$ is the length of the sliding strip 12 to measurement point n.

A segment that spans from n to n+1 on both the reference strip 14 and sliding strip 12 is provided as an example. On the side of the reference strip 14, the segment begins at $L_r[n]$ and ends at $L_r[n+1]$. Similarly, the corresponding sliding strip 12 extends from $L_s[n]$ to $L_s[n+1]$. The signed radius of curvature and the signed angular extent of the reference strip 14 segment can be found.

Recalling that:

$$r = t\frac{L}{L-L_s}$$

$$\theta_r = \frac{L-L_s}{t}$$

It can be seen that:

$$r[n] = t\frac{L_r[n+1] - L_r[n]}{(L_r[n+1] - L_r[n]) - (L_s[n+1] - L_s[n])}$$

$$\theta_r[n] = \frac{(L_r[n+1] - L_r[n]) - (L_s[n+1] - L_s[n])}{t}$$

A series of circular arcs of known length, angular extent, and radius of curvature is now known. This series can be pieced together to model the complete curve of the reference strip 14.

Figure 7:
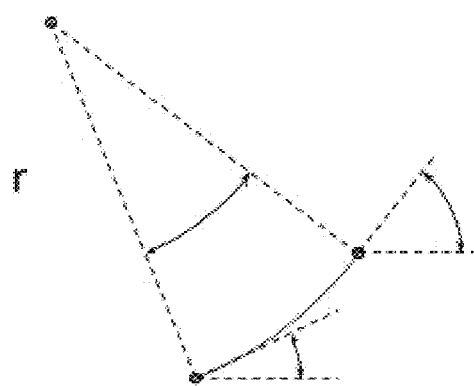
FIG. 7 is a diagram illustrating the calculations of a segment.

Consider a single arc as shown in FIG. 7. A starting angle $\phi[n]$ and an ending angle $\phi[n+1]$ which are tangent to the arc at its endpoints can be determined. It can be presumed that sequential segments connect smoothly—i.e. that the derivative is continuous at the point of connection. This is why the connection points are described by a single tangent angle.

The arc begins at a known starting point, (x[n], y[n]), and at an initial known angle of $\phi[n]$ and proceeds to an unknown ending point, (x[n+1], y[n+1]), at an unknown ending angle of $\phi[n+1]$. The change in angle from starting point to the ending point is just the turning of the segment angle.

$$\phi[n+1] = \phi[n] + \theta_r[n]$$

To find the x, y translation, the increment in x and y over the arc is added to the previous point. For convenience, the center of the radius of curvature of the arc is considered to be at the origin and used to calculate endpoint positions. The difference in these is then applied to the known starting point.

For this calculation, the angles from the center that form the arc are known. The normal to $\phi[n]$ is $$\phi[n] - \frac{\pi}{2}.$$

For an arc or positive radius of curvature, this gives the angle pointing out from the center of the radius of curvature. If the radius of curvature is negative, it points in the opposite direction. This results in a sign flip that is corrected by using the signed radius of curvature. The endpoints can then be found iteratively via these equations:

$$x[n+1] = x[n] + r[n]\cos\left(\phi[n+1] - \frac{\pi}{2}\right) - r[n]\cos\left(\phi[n] - \frac{\pi}{2}\right)$$

$$y[n+1] = y[n] + r[n]\sin\left(\phi[n+1] - \frac{\pi}{2}\right) - r[n]\sin\left(\phi[n] - \frac{\pi}{2}\right)$$

These equations can be slightly simplified using trig identities.

$$x[n+1] = x[n] + r[n](\sin(\phi[n+1]) - \sin(\phi[n]))$$

$$y[n+1] = y[n] + r[n](\cos(\phi[n]) - \cos(\phi[n+1]))$$

These equations describe the series of circular arcs that model the bend. A circular arc is typically described by its center ($C_x[n]$, $C_y[n]$), its radius of curvature r[n], a starting angle, and an angular extent $\theta_r[n]$.

The center of an arc segment can be found by starting at (x[n], y[n]), and following the radius to the arc center ($C_x[n]$, $C_y[n]$). The starting angle is found from the normal at the point (x[n], y[n]), which is $$\phi[n] - \frac{\pi}{2}.$$

The center is then:

$$C_x[n] = x[n] + r[n]\cos\left(\phi[n] - \frac{\pi}{2}\right) = x[n] + r[n]\sin(\phi[n])$$

$$C_y[n] = y[n] + r[n]\sin\left(\phi[n] - \frac{\pi}{2}\right) = y[n] - r[n]\cos(\phi[n])$$

Note that the use of the signed radius of curvature ensures following the normal to the center.

The starting angle is:

$$\left(\phi[n] - \frac{\pi}{2}\right)\text{sign}(r[n])$$

The sign is needed to flip the angle if the arc proceeds clockwise. The extent of the arc is $\theta_r[n]$, which is also a signed value.

Sensitivity to Measurement Error

Any real measurement of shift will be imperfect, making it important to understand how measurement errors impact the accuracy of the modelled curve. In jointed arms, noisy measurements of joint angles quickly accumulate, causing significant errors in the final position of the end effector. Measurement errors in the multibend sensor are more forgiving.

Consider the case of a single shift measurement error at the nth point. Compared to the ideal, the shifted point will cause an error in the radii of curvature of two adjacent segments. The error on one segment will be one direction, while the error on the other segment will be in the opposite direction, tending to cancel things out to first order. This property, of segment errors tending to create somewhat compensating errors holds in general and is a consequence of the shift measurements which give the total accumulated shift to that point.

To show the sensitivity to error, take the example of two successive segments with the coordinates:

$$x[0]=0, y[0]=0), (x[1], y[1]), (x[2], y[2])$$

Ideal measurements for $L_r[n]$ and $L_s[n]$ are given. However, $L_s[1]$ will be perturbed by a measurement error of $\delta$. How this error propagates to (x[2], y[2]) is then found.

In the unperturbed case (and noting that $\phi[0]=0$):

$$x[1] = x[0] + r[n](\sin(\phi[1]) - \sin(0)) = x[0] + r[n]\sin(\phi[1])$$

$$y[1] = y[0] + r[n](\cos(0) - \cos(\phi[1])) = y[0] + r[n](1 - \cos(\phi[1]))$$

$$r[n] = t\frac{L_r[n+1] - L_r[n]}{(L_r[n+1] - L_r[n]) - (L_s[n+1] - L_s[n])}$$

$$\theta_r[n] = \frac{(L_r[n+1] - L_r[n]) - (L_s[n+1] - L_s[n])}{t}$$

$$\phi[n+1] = \phi[n] + \theta_r[n]$$

Equally spaced measurement points, 1 unit apart are presumed.

$$L_r[n+1] - L_r[n] = 1 \text{ for all } n$$

Apostrophes are used to indicate the variables for the case with measurement error $\delta$ at $L_s[1]$. This allows the resulting angles with and without mid-point measurement error to be.

$$r[0] = t\frac{1}{1 - (L_s[1])}$$

$$r'[0] = t\frac{1}{1 - (L_s[1] + \delta)}$$

$$r[1] = t\frac{1}{1 - (L_s[2] - L_s[1])}$$

$$r'[1] = t\frac{1}{1 - (L_s[2] - L_s[1] - \delta)}$$

$$\theta_r[0] = \frac{1 - L_s[1]}{t}$$

$$\theta_r'[0] = \frac{1 - (L_s[1] + \delta)}{t}$$

$$\theta_r[1] = \frac{1 - (L_s[2] - L_s[1])}{t}$$

$$\theta_r'[1] = \frac{1 - (L_s[2] - L_s[1] - \delta)}{t}$$

$$\phi[0] = 0$$

$$\phi[1] = \theta_r[0] = \frac{1 - L_s[1]}{t}$$

$$\phi'[1] = \theta_r'[0] = \frac{1 - (L_s[1] + \delta)}{t}$$

$$\phi[2] = \phi[1] + \theta_r[1] = \frac{1 - L_s[1]}{t} + \frac{1 - (L_s[2] - L_s[1])}{t} = \frac{2 - L_s[2]}{t}$$

$$\phi'[2] = \phi'[1] + \theta_r'[1] = \frac{1 - (L_s[1] + \delta)}{t} + \frac{1 - (L_s[2] - L_s[1] - \delta)}{t} = \frac{2 - L_s[2]}{t}$$

This shows that the ending angle after two arcs is unimpacted by a misreading in the middle point. The angle error does not propagate.

The error in the point locations are considered.

$$x[n+1] = x[n] + r[n](\sin(\phi[n+1]) - \sin(\phi[n]))$$

$$y[n+1] = y[n] + r[n](\cos(\phi[n]) - \cos(\phi[n+1]))$$

$$x[1] = r[0](\sin(\phi[1])) = t\frac{1}{1 - (L_s[1])}\sin\sin\left(\frac{1 - L_s[1]}{t}\right)$$

-continued $$y[1] = r[0](1 - \cos(\phi[1])) = t\frac{1}{1-(L_s[1])}$$

$$x'[1] = r'[0](\sin(\phi'[1])) = t\frac{1}{1-(L_s[1]+\delta)}\sin\sin\left(\frac{1-(L_s[1]+\delta)}{t}\right)$$

$$y'[1] = r'[0](1 - \cos(\phi'[1])) = t\frac{1}{1-(L_s[1]+\delta)}$$

$$x[2] =$$

$$x[1] + r[1](\sin(\phi[2]) - \sin(\phi[1])) = t\frac{1}{1-(L_s[1])}\sin\sin\left(\frac{1-L_s[1]}{t}\right) +$$

$$t\frac{1}{1-(L_s[2]-L_s[1])}\left(\sin\left(\frac{2-L_s[2]}{t}\right) - \sin\left(\frac{1-L_s[1]}{t}\right)\right)$$

$$y[2] = y[1] + r[1](\cos(\phi[1]) - \cos(\phi[2])) =$$

$$t\frac{1}{1-(L_s[1])} + t\frac{1}{1-(L_s[2]-L_s[1])}\left(\cos\left(\frac{1-L_s[1]}{t}\right) - \cos\left(\frac{2-L_s[2]}{t}\right)\right)$$

$$x'[2] = x'[1] + r'[1](\sin(\phi'[2]) - \sin(\phi'[1])) =$$

$$t\frac{1}{1-(L_s[1]+\delta)}\sin\sin\left(\frac{1-(L_s[1]+\delta)}{t}\right) +$$

$$t\frac{1}{1-(L_s[2]-L_s[1]-\delta)}\left(\sin\left(\frac{2-L_s[2]}{t}\right) - \sin\left(\frac{1-(L_s[1]+\delta)}{t}\right)\right)$$

$$y'[2] = y'[1] + r'[1](\cos(\phi'[1]) - \cos(\phi'[2])) = t\frac{1}{1-(L_s[1]+\delta)} +$$

$$t\frac{1}{1-(L_s[2]-L_s[1]-\delta)}\left(\cos\left(\frac{1-(L_s[1]+\delta)}{t}\right) - \cos\left(\frac{2-L_s[2]}{t}\right)\right)$$

Using these equations, the endpoint error under different conditions can be plotted. It is clear that position error at the end of the first segment is somewhat compensated for by an oppositely signed error in the next segment.

While the embodiment and examples discussed above uses arcs in performing the analysis, other measurement techniques and analyses may be employed. In an embodiment, ellipses are used for approximating the curves. In an embodiment, analysis of the may be performed using parabolas. In an embodiment, splines are used for approximating a curve. In an embodiment, a polynomial function is used for approximating the curve. In an embodiment, all of the methodologies discussed herein are used in approximating the curve.

Another possible model of a curve is to represent it as a series of connected straight linear segments.

Figure 8:
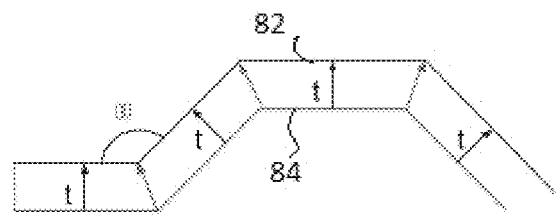
FIG. 8 is a diagram illustrating using a linear segment analysis for the curves.
Figure 9:
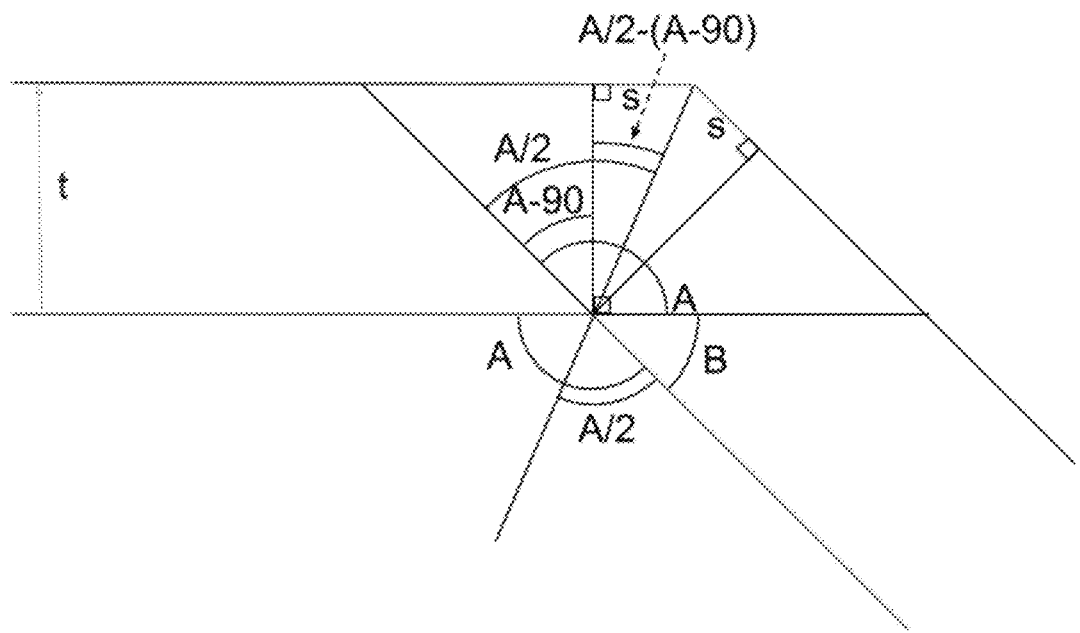
FIG. 9 is a diagram illustrating the determination of angles in the linear segment analysis.

Referring to FIGS. 8 and 9, for a piecewise linear model, the bends are presumed to be perfectly sharp, and occur only at fixed intervals on a reference strip 84. The sliding strip 82 will be presumed to conform to a fixed distance from the reference strip 84. This will create corresponding sharp bends for each bend of the reference strip 84. Bending towards the reference strip 84 will mean that extra length will be needed on the sliding strip 82 to conform to the new shape. Similarly, bending towards the sliding strip 82 will take less length to conform.

The calculation is begun by calculating the extra length required on the sliding strip 82 given a bend toward the reference strip 84. Looking towards FIG. 9, the multibend sensor has a bend of angle A. The vertically opposite angle is also A. The extra length of the sliding strip 82 needed to conform to the bend is shown as 2 s. The two bend points bisect the bend angle. The vertically opposite angle is also A/2. With the right angle construction, the A−90 angle is found by subtracting the right angle. Finally the angle opposite s is computer as A/2−(A−90). The tangent of this angle is equal to the opposite side length (s) divided by the adjacent side length (t).

$$\tan(A/2-(A-90))=s/t$$

$$s=t^*\tan(90-A/2)$$

$$s=t^*\cot(A/2)$$

And for the total length added:

$$2s=2t^*\cot(A/2)$$

This formula is also correct for when the bend angle exceeds 180, and bends up towards the sliding strip 82. In this case the additional length is negative.

For convenience, the bending angle, B, can be defined relative to no bend being 0.

$$B=180-A$$

$$A=180-B$$

Substituting in:

$$s=t^*\tan(90-B/2)=t^*\tan(90-(180-B)/2)=t^*\tan(B/2)$$

$$2s=2t^*\tan(B/2)$$

Given a measurement of shift, the angle that would have given rise to it is calculated.

$$B=2\arctan(s/t) \text{ where s is the half shift.}$$

Like the circular arc model, this piecewise linear model still has the general behavior of measurement error in one shift measurement creating a complimentary error in the next, partially canceling out the impact of potential additive error.

Consider an ideal measurement vs one where there is measurement error in the first segment.

Ideal measurements: s1 and s2
Measurements with error: s1+d, s2−d $$B1=2\arctan(s1/t)$$

$$B2=2\,\text{acrtan}(s2/t)$$

The resulting angle of the last segment is simply the sum of the angle to that point.

$$B\text{total}=B1+B2=2\arctan(s1/t)+2\arctan(s2/t)$$

Repeating the calculation with measurement error:

$$B\text{total\_err}=2\arctan(s1/t+d/t)+2\arctan(s2/t-d/t)$$

These total bends are not the same, however, it can be shown via series expansion around d=0 that the errors cancel to first order.

Physical Implementations

The mechanism of measuring shift between two bending members with fixed spacing can be accomplished using different sensing techniques in conjunction with the reference strip and the sliding strips.

Capacitive Sensing Techniques

Capacitive sensing can be used with a multibend sensor and is the methodology discussed above with respect to FIGS. 1-3. Electrodes can be patterned on standard flexible printed circuit boards (PCB) when creating the reference strip and the sliding strip. The capacitance through the spacer can be measured, and relative position determined. For example, looking to FIG. 10, a pattern of interdigitated electrodes 20 allows one to perform differential measurements by comparing the capacitance of overlapping electrodes 20 to determine relative shift. The differential nature of this measurement makes it highly insensitive to various types of error. In addition to the electrode pattern shown in FIG. 10, other electrode patterns can be implemented that will further provide measurements that can help determine the overall movement and shape of the multibend sensor.

Figure 10:
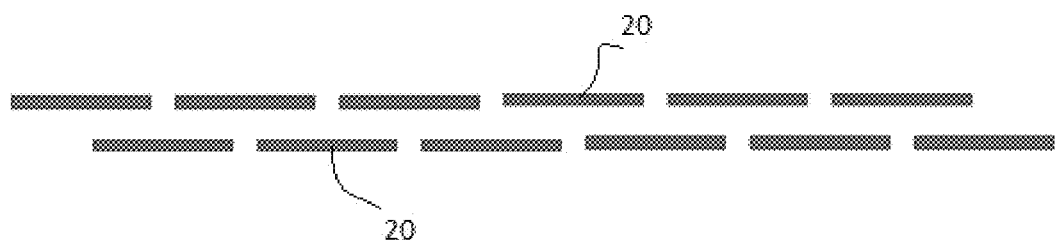
FIG. 10 is a diagram illustrating the spaced electrodes.

Still referring to FIG. 10, a plurality of the electrodes 20 are adapted to transmit signals and a plurality of the electrodes 20 are adapted to receive signals from the electrodes 20 that are transmitting signals. In an embodiment, the electrodes 20 adapted to transmit signals and the electrodes 20 adapted to receive signals may be switched or alternated depending on the implementations. In an embodiment, an electrode 20 adapted to transmit a signal may at a different time also be adapted to receive a signal. Received signals are used in order to determine movement of one strip with respect to the other strip.

In an embodiment, orthogonal frequency division multiplexing can be used with a multibend sensor employing a plurality of electrodes 20 that are adapted to receive and transmit orthogonal signals. In an embodiment, unique frequency orthogonal signals are used. In an embodiment, a unique frequency orthogonal signal is transmitted on each of the electrodes 20 that is transmitting. Electrodes 20 that are adapted to receive signal may receive the transmitted signals and process them in order to obtain information regarding the relative shift of the reference strip with respect to the sliding strip. This can then be used to determine the shape of the curve formed by the multibend sensor.

In general, the curvature of multiple dimensions can be determined by forming a mesh of reference strips and sliding strips with each multibend sensor determining its own respective curve. After the curve of each multibend sensor is determined the entire curvature of a plane can be modeled. In an embodiment, a plurality of multibend sensors may be placed on a three dimensional object that is subject to various deformation across its 3D surface. The plurality of multibend sensors may be able to accurately determine the curving deformation of a 3D object after reconstructing curvature taken from each of the multibend sensors.

In another embodiment, the strips are replaced with fibers that are flexible in 3 dimensions. These fibers are then packed around a central reference fiber such that the outer sliding fibers move relative to the reference fiber when bent. In embodiment, spacers maintain a constant spacing between all the fibers. The relative shifts can be measured by a variety of means, including via patterned electrodes along the fiber.

In an embodiment the sensor may be created from narrow sheets that more closely resemble a flexible wire, being able to flex outside of the plane. If two of these devices are held together, sensing in orthogonal directions, flexing in and out of the plane can be measured.

Figure 11:
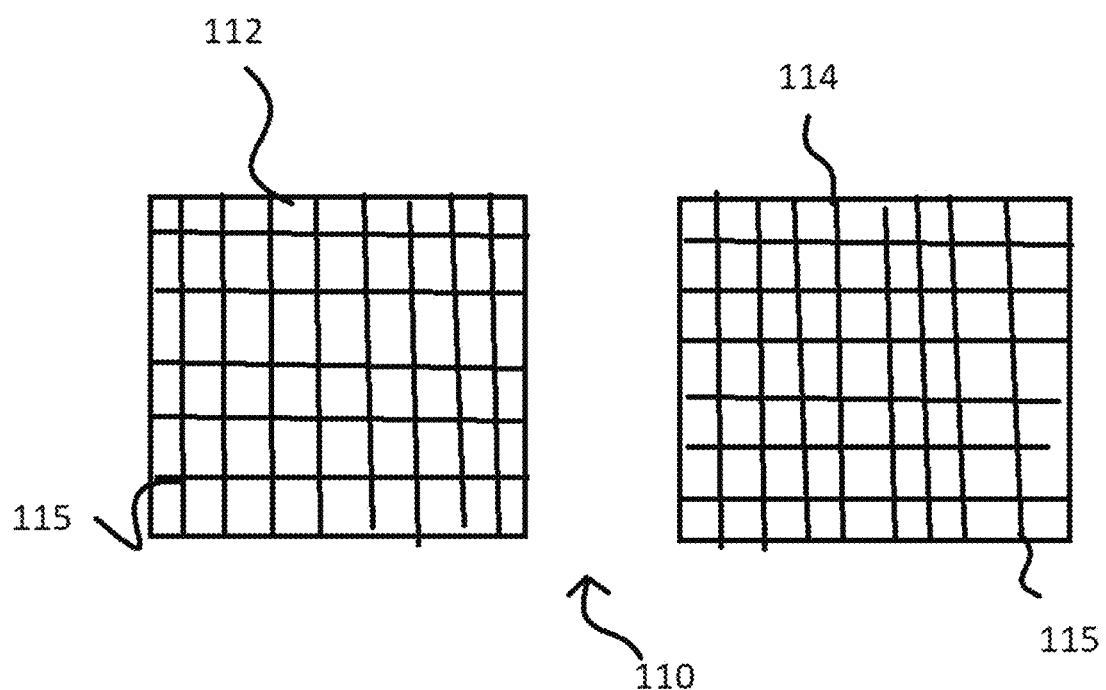
FIG. 11 is a diagram illustrating a multiplanar multibend sensor.

Another embodiment is shown in FIG. 11. This embodiment provides a multibend sensor 110 that is able to determine curvature in more than one planar direction. There is a sliding plane 112 and a reference plane 114. In FIG. 11 the planes are not shown on top of each other however it should be understood that this is for ease of viewing the planes sliding plane 112 and the reference plane 114 are positioned with respect to each other in a similar manner in which the strips discussed above are positioned. Electrodes 115 are placed on the sliding plane 112 and the reference plane 114. In FIG. 11, the electrodes 115 are formed as rows and columns. In an embodiment, the electrodes are formed as pads. In an embodiment, the electrodes are formed as dot antennas. There may additionally be a spacer plane placed between the sliding plane 112 and the reference plane 114 in order to establish a distance between the sliding plane 112 and the reference plane 114. In an embodiment, the reference plane 114 and the sliding plane 112 are implemented without a spacer layer with the electrodes are 115 placed on the outward facing surfaces with the substrates of the planes functioning as a spacer layer. Furthermore, while there may be electrodes 115 placed on both planes, there may be transmitting electrodes placed on the sliding plane 112 and the reference plane 114 and receiving electrodes located at an interstitial region between the two planes. Also, the electrodes 115 can be either transmitting or receiving.

Still referring to FIG. 11, the sliding plane 112 and the reference plane 114 are flexible planes that are able to bend. The reference plane 114 and the sliding plane 112 are attached at various attachment points. Attachment points may be located at any location between the planes provided that they establish a reference location by which to ascertain the movement of one plane with respect to the other. In an embodiment, the attachment point may be the center location of the planes. In an embodiment, there are more than one attachment point from which relative movement of the planes is established. In an embodiment the planes are secured to each other at an edge. In an embodiment, the planes are secured at multiple points along the edge. In an embodiment, the planes are secured at points along an edge and within the area of the planes.

Figure 12:
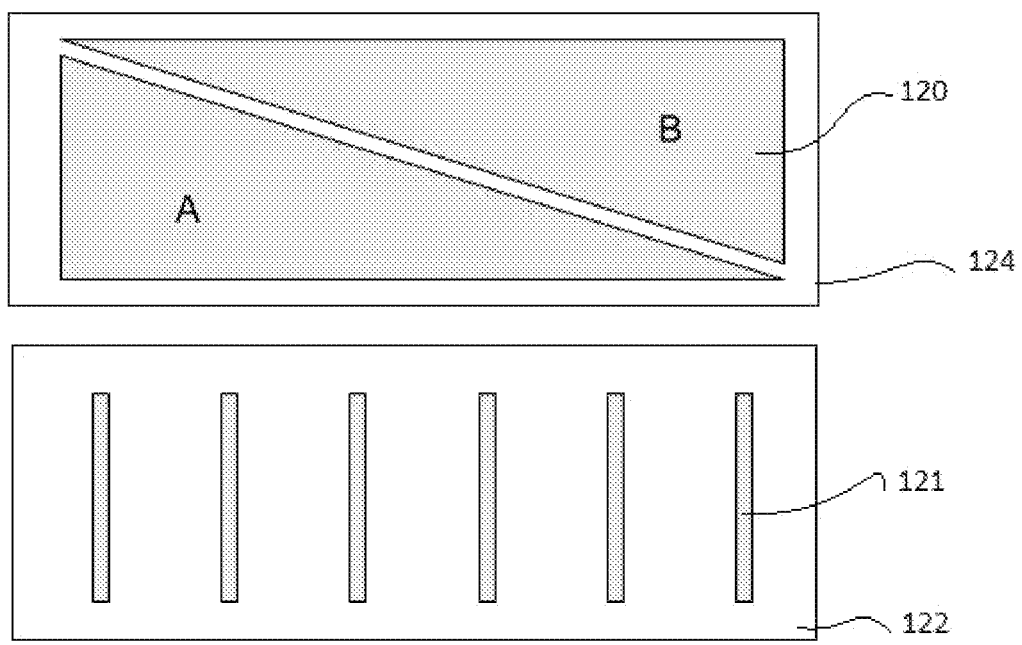
FIG. 12 is a diagram of a multibend sensor employing triangular electrodes and rectangular electrodes.
Figure 13:
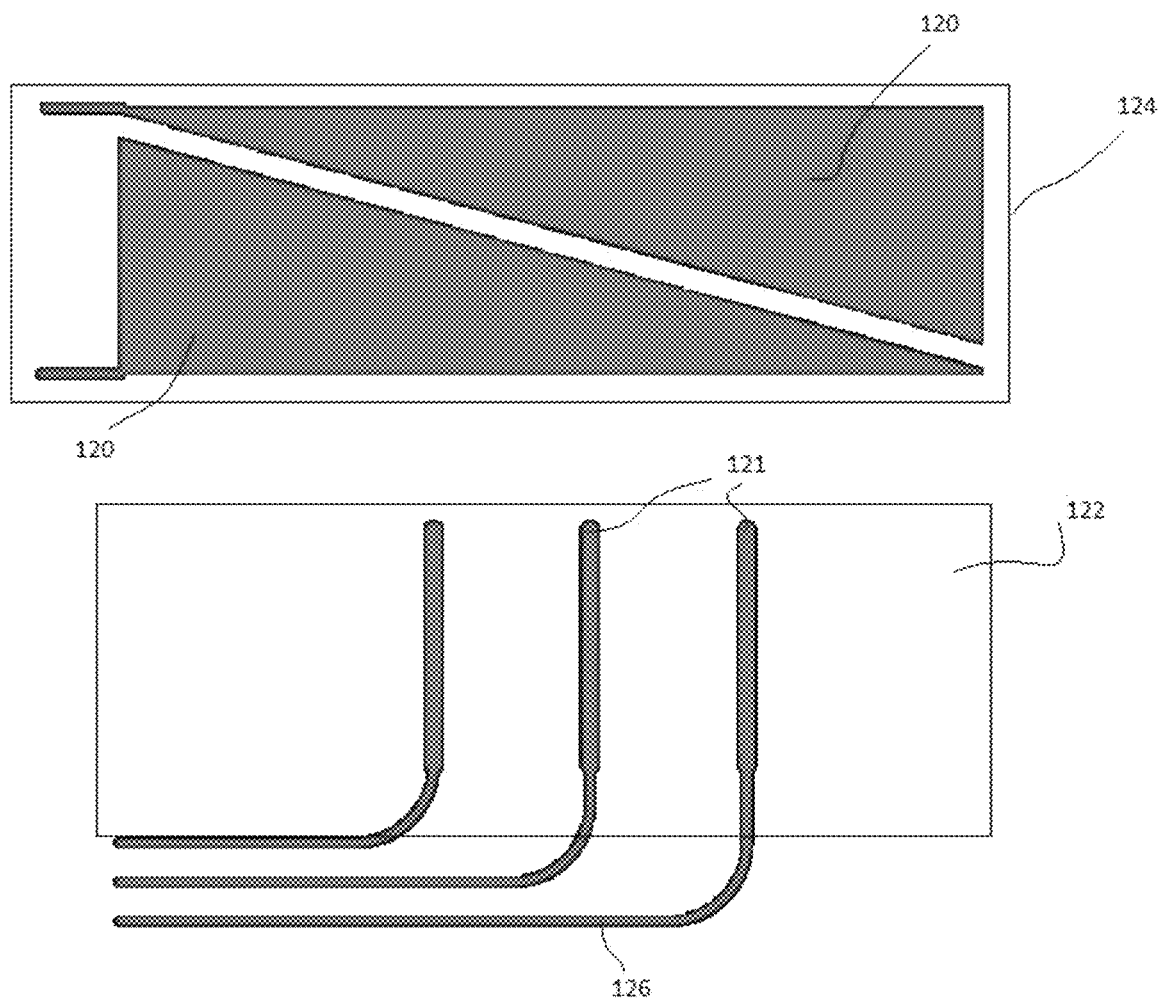
FIG. 13 is another diagram of a multibend sensor employing triangular electrodes and rectangular electrodes further illustrating connections.

Turning to FIGS. 12 and 13, another embodiment of a capacitive electrode design to measure relative shift is shown. While multilayer flex circuits are widely available, there are certain limitations to design that may be imposed. A common restriction is to not allow vias on bending sections. Therefore, patterns which do not require interlayer connections in bending areas are sometimes preferred.

FIG. 12 shows two triangular electrodes 120 that form the reference strip 124, and a series of rectangular electrodes 121 formed on the sliding strip 122. By measuring the relative capacitance to the A electrode 120 to the capacitance to the B electrode 120 for each of the rectangular electrodes 120 on the sliding strip 122, the relative position of the rectangular electrodes 120 can be determined.

This pattern shown in FIGS. 12 and 13 does not require multiple layer connections. On the reference strip 124, connections can be directly made from either end. The rectangular electrodes 121 on the sliding strip 122 can be made via bus 126 as shown in FIG. 13. In an embodiment, shielding can be employed around the rectangular electrodes 121 and the triangular electrodes 120. Shielding can assist in mitigating interference. Electrodes that are transmitting can be surrounded by ground and receiving electrodes can be driven with an active shield in order to mitigate interference.

The design shown in FIGS. 12 and 13 is sensitive to slight rotations between the reference strip 124 and the sliding strip 122. For example, if the spacing is greater on the top versus the bottom, it may cause a systematic error. This can be corrected by calibration. Sensitivity can also be ameliorated by using a less sensitive pattern.

Figure 14:
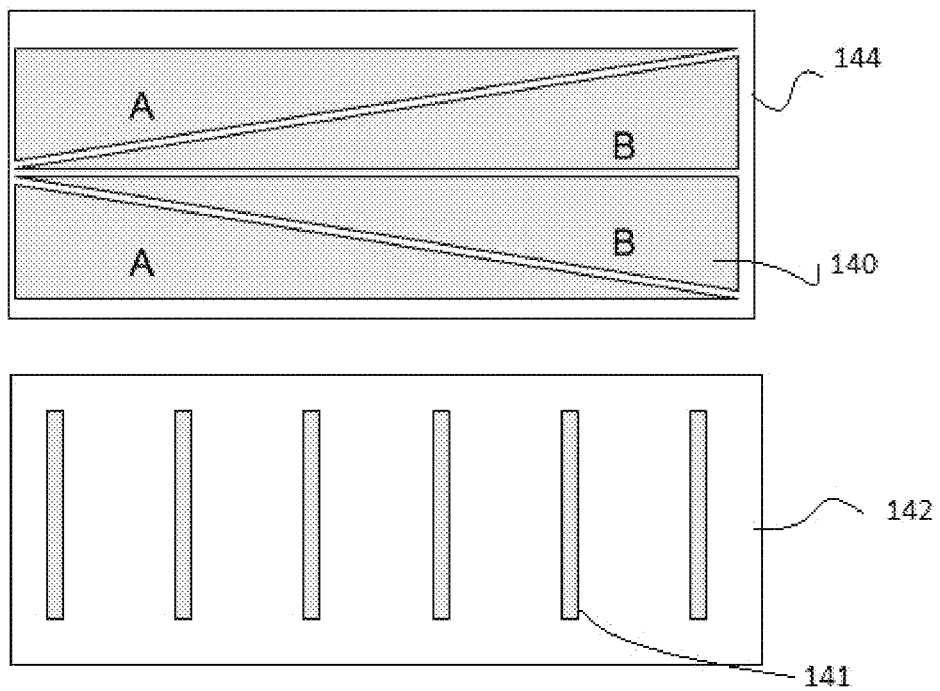
FIG. 14 is a diagram of a multibend sensor employing triangular electrodes and rectangular electrodes.

An example of a pattern with reduced sensitivity is shown in FIG. 14. The pattern shown in FIG. 14 employs additional triangular electrodes 141 placed on the reference strip 144. Rectangular electrodes 141 are placed on the sliding strip 142. The electrode pattern shown in FIG. 14 is symmetric about the centerline of the reference strip 144. This reduces the sensitivity as compared to the pattern shown in FIG. 12. The reduced sensitivity occurs because the triangular electrode 141 is further away on one side and closer on the other side. This distance roughly balances out the impact of any tilt that may exist.

Figure 15:
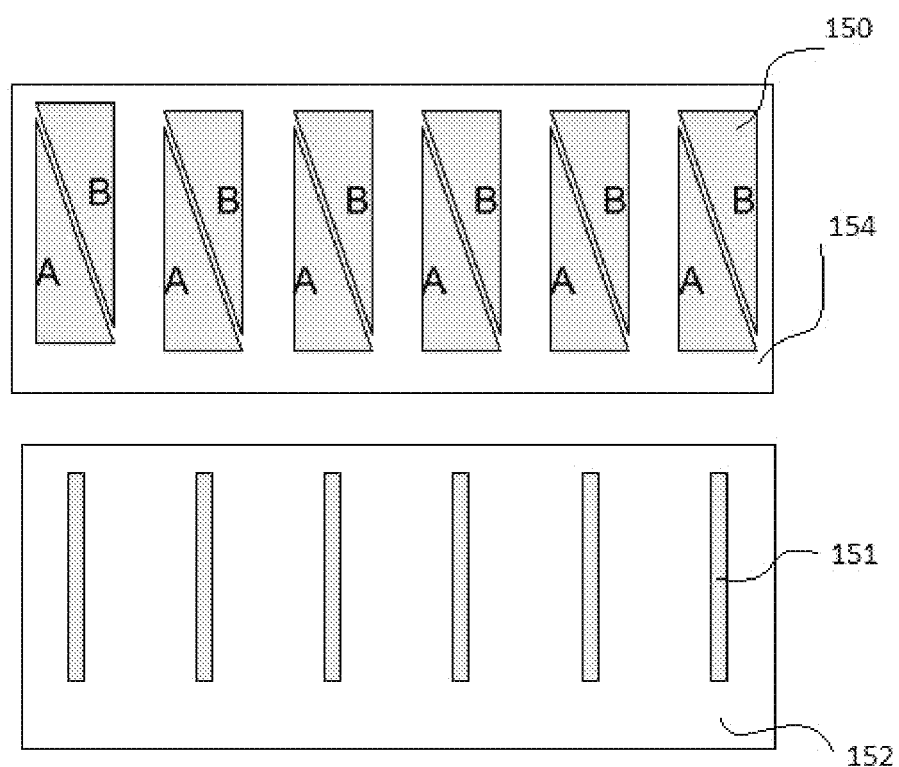
FIG. 15 is another diagram of a multibend sensor employing triangular electrodes and rectangular electrodes.

FIG. 15 shows another embodiment of sensor electrodes. FIG. 15 shows an arrangement of a reference strip 154 and sliding strip 152. The reference strip 154 has a plurality of triangular electrodes 150. The sliding strip 152 has a plurality of rectangular electrodes 151. In comparison to the electrode pattern shown in FIG. 12, the pattern in FIG. 15 replicates that arrangement of triangular electrodes 150. The angled pattern is replicated on a smaller scale in the neighborhood of each measurement to improve resolution. The sensor pattern shown in FIG. 15 can also be combined with shielding and symmetry techniques.

Figure 16:
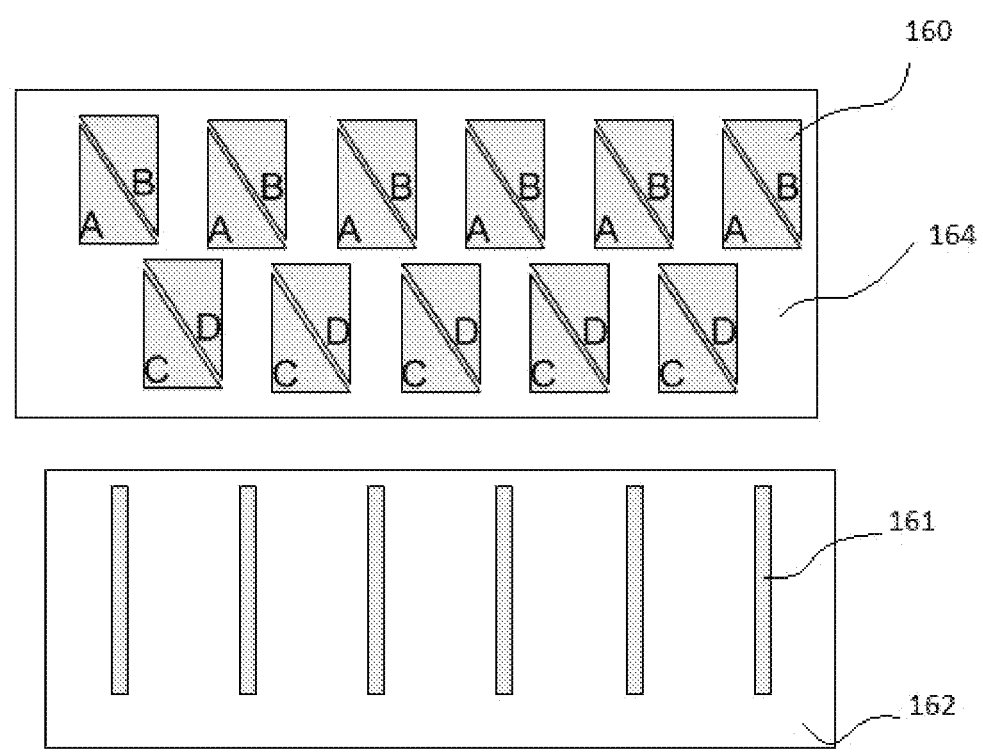
FIG. 16 is another diagram of a multibend sensor employing triangular electrodes and rectangular electrodes.

FIG. 16 shows another embodiment of sensor electrodes. FIG. 16 shows an arrangement of a reference strip 164 and sliding strip 162. The reference strip 164 has a plurality of triangular electrodes 160. The sliding strip 162 has a plurality of rectangular electrodes 161. In comparison to the electrode pattern shown in FIG. 12, the pattern in FIG. 16 replicates that arrangement of triangular electrodes 160. The angled pattern is replicated on a smaller scale in the neighborhood of each measurement so as to improve resolution. The sensor pattern shown in FIG. 16 can also be combined with shielding and symmetry techniques. When shifting causes a rectangular electrode 161 to get near the end of a triangular electrode 160, some nonlinearity will result. A way to address this is to use multiple sets of the triangular electrodes 160. The sets are shifted so that when a rectangular electrode 161 is near an edge on one triangular electrode 160, it is not at an edge on another of the triangular electrode 160.

Optical

In addition to capacitive based sensing, multibend sensors can be created using optical techniques rather than capacitive. Instead of interdigitated electrodes, optical transmitters and receivers can be used. Signals can be transmitted through an optically transmissive spacer located between a reference strip and sliding strip. Waveguide techniques permit the electronics to be placed at one end, rather than distributing them along the sensor.

Using standard flex circuit techniques, it is possible to place standard electro-optic components such as LEDs and photodiodes on a flexible strip. However, because these components are not in and of themselves flexible, local stiffening at the measurement point may be needed. Certain techniques may be used to work around the issue of local stiffening. In general, flexible electronics can be applied to the manufacture of multibend sensors (e.g. doing local electric field sensing, and reporting data back via a shared bus). In particular, the availability of OLEDs and other optic devices in a flexible form makes it possible to build distributed optical encoders along a flexible strip.

Flexible waveguides may also be employed to bring the optical signal to and from the measurement points distributed along the strips. In this way, the optoelectronics can be gathered at one location. For example the optoelectronics can be placed at the end where the strips are joined. At this location a rigid PCB can hold the electro-optic components.

Additionally, to cut down on the required number of optical connections, multiplexing techniques can be employed. For example, each sense location could employ optical filters so that different colors of light, different polarizations, or some combination of these are active at different locations along the multibend sensors, and can be distinguished at the end with the opto-electronics.

These systems have a path for light to travel from one strip to the other. This can be accommodated several different ways. In an embodiment, the spacer may be made from transparent materials. In an embodiment, slots may be provided in the neighborhood of the measuring spots. In an embodiment, the spacer may maintain an air gap between the strips. In an embodiment, the optical fibers may have nicks that permit light to bleed from one cable to another. In an embodiment, there may be bundles of optical fibers that are tied in the middle wherein the relative shift of both ends of the bundles are able to be determined.

Figure 17:
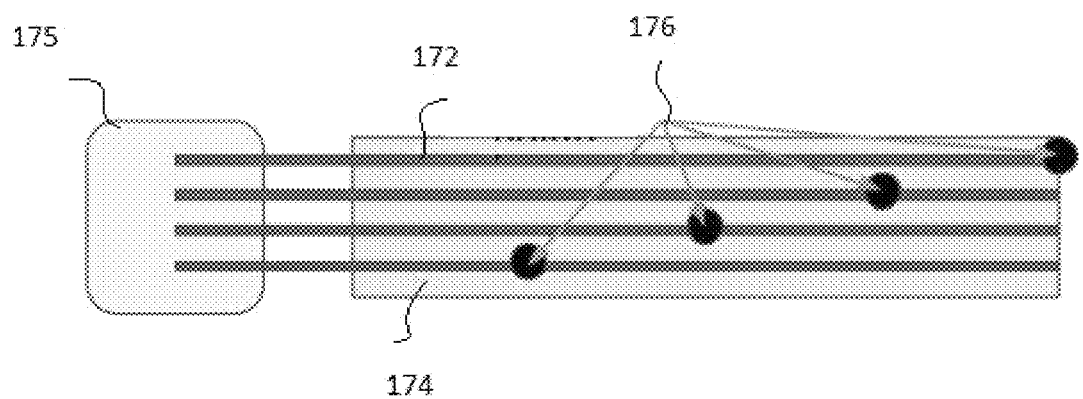
FIG. 17 is a diagram showing the use of parallel strips with a camera chip.

Referring to FIG. 17, inexpensive camera chips also can be used to make multibend sensors. These chips could be used at various points along the strips so as to measure shift. Still referring to FIG. 17, multiple, parallel sliding strips 172 are used that attach to a reference strip 174 at staggered attachment points 176. The ends of these sliding strips 172 can then extend to be observed by a camera chip 175. A single camera can thus track the motion of multiple slide strips 172 with high precision, effectively giving the same result as measuring the shift at different locations.

While flexible electronics are an option, there are other options for distributing optoelectronics along a flexible strip. In an embodiment, a rigid PCB may be attached to a flexible strip via elastic members. In this way, the strip can still bend freely, while the floating electro-optic module looks toward the encoder markings on the other flexible strip. To help maintain alignment, the electro-optic module can be designed to have a larger optical area that looks through a smaller aperture in the flexible strip. Even if the rigid PCB slightly wiggles with respect to the strip, the measurement will always be done with respect to the aperture in the strip.

Figure 18:
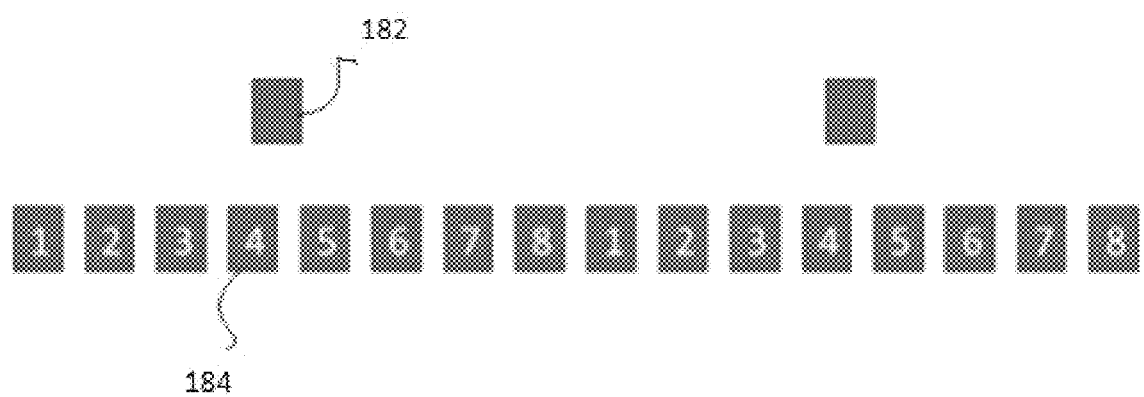
FIG. 18 is a diagram showing an electrode pattern for a sensor that is able to determine wrapping.

When sensing shift, there is a question of how much shift must one sense before running out of range. Looking to the arrangement of receiving electrodes 182 and transmitting electrodes 184 shown in FIG. 18 an example of shifting range can be explained. In this case, there are a small number of receiving electrodes 182 that are placed on a sliding strip, and a larger number of transmitting electrodes 184 placed on a reference strip. Instead of providing unique signals on every transmitting electrode 184, signals are reused periodically. Each of the numbered transmitting electrodes 184 representing a different signal. If the shift is limited to the region of one set of transmitting electrodes 184, the position can be uniquely determined. If the shift is greater than this, the shift reading is not uniquely determined by the closest transmitting electrode 184. In this instance it could have shifted so much as to have wrapped into the next set of transmitting electrodes 184. Because a sequence of measurements is made along the strips, the combined shift from earlier segments can be seen and is likely to indicate that a wrap has occurred. Because incremental unwrapping can occur, the constraint is not on any particular receiving electrode 182 staying within range of one set of transmitting electrodes 184. It is only limited by the ability to unwrap. If it is known that the number of transmitting electrodes 184 between successive receiving electrodes 182 is limited to +/−half the number of receiving electrodes 182 nominally between transmitting electrodes 184 one can uniquely determine the position of the next segment because it is known which transmitting electrodes 184 could be within range of the previous segment. More sophisticated techniques can extend this even further for example, by making assumptions about higher order derivatives. Although this technique is explained in the context of a capacitive sensor, the same technique can be applied to other embodiments. Using the optical multistrip setup, instead of just detecting an end, the strip can have repeated variations which are detected and analyzed to find a precise position. It is possible to use calibration targets with many edges to allow the positions to be determined by combining data all of them.

Other Methodologies

Above, capacitive and optical techniques were discussed, however, other mechanisms may be employed. For example, similar to a potentiometer, one strip can serve as a distributed resistor, and the other may have multiple wipers that make contact at numerous points along the resistive strip. The voltage at each wiper can be arranged to indicate the relative position along the resistive strip. A resistive strip is located on one strip, and a voltage placed across it. This creates a voltage gradient along the strip that is position dependent. Wipers along the top strip make sliding contact with the strip, sensing the voltage at their location. The wrapping detection discussed above can be achieved by having a separate potentiometer formed in the region of each wiper to allow more precise measurements. Mechanically, the wipers could also play a role in maintaining the spacing between the layers since they are spacers in and of themselves.

An improvement on the above design is rather than having a single resistive stripe along the strip, separate ones may be placed in the neighborhood of each wiper. Then each smaller resistive stripe could have the entire voltage gradient over a much smaller displacement, greatly increasing the resolution of the measurement. It should be noted that the number of connections to the strip with the resistive stripes is still only two.

Rather than mechanical wipers, other methods can be employed to create shift-dependent resistivity changes. For example, magneto-resistive materials change resistance in the presence of a magnetic field. A resistive trace, running parallel to a conductor could be effectively bridged at different locations including magneto-resistive material between these traces, which can be selectively made more conductive by a magnet on the other strip.

Another embodiment employs a series of magnets on one strip and Hall effect sensors on the other in order to measure shift. Time domain techniques may also be utilized to measure length. Time domain reflectometry techniques in either the electrical, optical or acoustic domain can be used to measure shift at multiple points. To use these, the measurement points create a path for signal to return. Magnetostrictive position transducer methods may also be used to measure shift.

In an embodiment, inductive proximity sensing can be employed. The inductance of a coil will change in response to certain materials being within proximity to them. For example, in an embodiment, one strip carries a series of coils, while the other has sections of different magnetic permeability that are detected by the coils. The detection can be done a number of ways, including noting the change in inductance of each coil independently, or looking for the change in coupling among different coils. It is also possible to have coils on both strips, and measure the coupling between them. Linear Variable Differential Transformers (LVDTs) can be straightforwardly applied to this type of measurement.

In an embodiment, electromagnetic coupling can be utilized using radio frequency (RF) coupling between the strips.

In an embodiment, multibend sensors are designed for remote interrogation via RF. A simple tank circuit (LC) is used where either the L or C are dependent on the relative shift between strips. This type of circuit can be created on the strips using only patterning of conductive material. The resonant frequency of the tank circuit is dependent on relative shift, and can be read remotely using standard RFID techniques. The strips can be designed so as to contain multiple resonances that are each dependent on the local relative shift. If the resonances are reasonably separated in frequency, a remote frequency scan can reveal the change in each resonance independently. With the addition of active components, other techniques, such as time domain multiplexing can be employed to read the shift over multiple points.

Magnetic sensors (Hall effect, Giant Magnetoresistive, etc.) can be used to measure local magnetic field. A pattern of magnetization of one strip could be detected on the other to determine relative shift at many points. Magnetic circuits can be employed to bring the flux measurement to a convenient physical location. High magnetic permeability material serves to channel the flux similar to a conductive wire carrying electric current. Using these techniques, a number of magnetic sensors can be positioned on the conjoined end of the strips, making measurements at various points along the strips.

Magnetostrictive transducers have been employed for measuring position in harsh industrial environments. The position of a moving magnet is determined by pulsing current in a magnetostrictive element, which causes a mechanical impulse to be generated in the element in the region of the magnet. The time for this impulse to propagate back to a measurement point is a function of the position of the magnet. In an embodiment, magnets are placed on one strip, and magnetostrictive material is placed on the other.

Analogous techniques can be employed using photoconductive materials. A light on the sliding strip can shift the location of bridging. This could be an LED or other light source mounted on the strip, or a simple aperture through which a separate light source is allowed to selectively pass.

Some of the measurement error propagation properties of the multibend sensor can be obtained on more traditional arm/encoder systems through mechanical means. Parallel linkages are often used to maintain the parallelity of two members.

Figure 19:
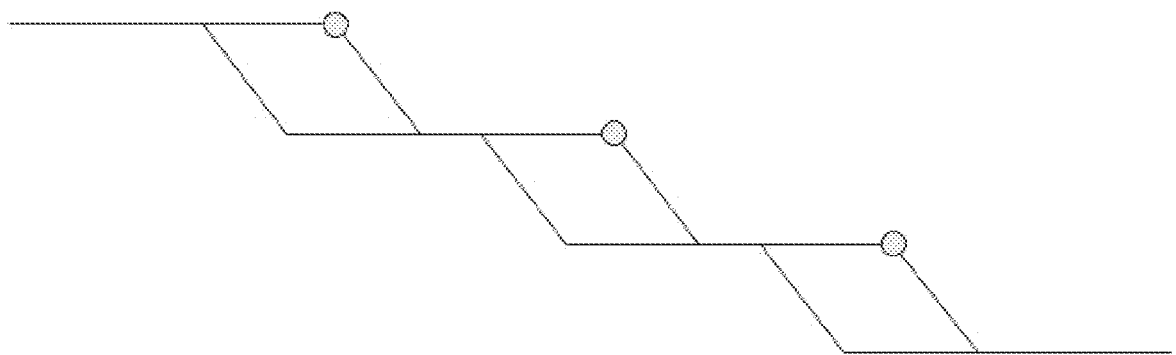
FIG. 19 is a diagram of mechanical multibend sensor.

FIG. 19, shows three sets of parallel linkages that guarantee that the horizontal lines remain parallel to each other. The dots represent encoders. The angle measured at each encoder is always with respect to the top line. In this way, measurement errors at each encoder do not propagate in measuring the absolute exit angle at each encoder. Various combinations of gears, belts and other linkages can be employed to similar effect.

The above discussed multibend sensors provide curvature data along its length. This data can be used in more sophisticated ways to give more detailed models. For example, one can interpolate or fit a higher order function to model the change in curvature along the sensor, and thus create a model with effectively many more segments. One could also change the underlying model of a segment from a circular arc to a different functional form.

The above described embodiments of the multibend sensor can accurately determine the shape of a curve or curved surface. Some applications of this technique may be in determining the positioning of robotics systems. In an embodiment the multibend sensor is used for pliable interfaces. In an embodiment the multibend sensor is used for human joint motion rehabilitation. In an embodiment the multibend sensor is used for human joint motion in virtual reality. In an embodiment, the multibend sensor is used for determining curvature of a back, movement of a head, or bending of legs. In an embodiment the multibend sensor is used for measuring complex curves. In an embodiment the multibend sensor is used for complex vibration understanding and active control. In an embodiment the multibend sensor is used for automotive, tires and seat deformation. In an embodiment the multibend sensor is used for posture monitoring. In an embodiment the multibend sensor is used for expressive musical instrument interfaces. In an embodiment the multibend sensor is used for tank/pressure bladder monitoring for deformations such as bubbling out (e.g. monitoring planes, submarines etc.).

The multibend sensor may also be used in understanding the shape of a pressurized system. For example, airplanes with pressurized cabins undergo significant stress and deformation as they are repeatedly pressurized and depressurized. If a particular area becomes weakened through repeated stress, it will begin to bubble out (or in depending on which side you are looking at) relative to other areas. The multibend sensor is employed so as to detect this for understanding the rate of system fatigue, and where failures may be imminent. Submarines, holding tanks, and all sorts of pressurized containers have similar issues that can benefit from the application of the multibend sensor. In an embodiment, the multibend sensor is used in assisting with oil and gas exploration when determining the curvature of bits.

Other mechanical systems that deform under load can also benefit from the multibend sensor. Another advantage of the multibend sensors described above is that the precision arises from geometric relationships rather than from electrical properties that are susceptible to changes due to environmental condition and are subject to aging and wear, this makes the disclosed multibend sensors suitable for monitoring bridges, support beams, etc. over the life of the structure.

Another advantage of the multibend sensors described above is that the precision arises from geometric relationships rather than from electrical properties that are susceptible to changes due to environmental condition and subject to aging and wear. Implementations of this application may employ principles used in implementing orthogonal frequency division multiplexing sensors and other interfaces disclosed in the following: U.S. Pat. Nos. 9,933,880; 9,019,224; 9,811,214; 9,804,721; 9,710,113; and 9,158,411. Familiarity with the disclosure, concepts and nomenclature within these patents is presumed. The entire disclosure of those patents and the applications incorporated therein by reference are incorporated herein by reference. This application may also employ principles used in fast multi-touch sensors and other interfaces disclosed in the following: U.S. patent application Ser. Nos. 15/162,240; 15/690,234; 15/195,675; 15/200,642; 15/821,677; 15/904,953; 15/905,465; 15/943,221; 62/540,458, 62/575,005, 62/621,117, 62/619,656 and PCT publication PCT/US2017/050547, familiarity with the disclosures, concepts and nomenclature therein is presumed. The entire disclosure of those applications and the applications incorporated therein by reference are incorporated herein by reference.

As used herein, and especially within the claims, ordinal terms such as first and second are not intended, in and of themselves, to imply sequence, time or uniqueness, but rather, are used to distinguish one claimed construct from another. In some uses where the context dictates, these terms may imply that the first and second are unique. For example, where an event occurs at a first time, and another event occurs at a second time, there is no intended implication that the first time occurs before the second time, after the second time or simultaneously with the second time. However, where the further limitation that the second time is after the first time is presented in the claim, the context would require reading the first time and the second time to be unique times. Similarly, where the context so dictates or permits, ordinal terms are intended to be broadly construed so that the two identified claim constructs can be of the same characteristic or of different characteristic. Thus, for example, a first and a second frequency, absent further limitation, could be the same frequency, e.g., the first frequency being 10 Mhz and the second frequency being 10 Mhz; or could be different frequencies, e.g., the first frequency being 10 Mhz and the second frequency being 11 Mhz. Context may dictate otherwise, for example, where a first and a second frequency are further limited to being frequency-orthogonal to each other, in which case, they could not be the same frequency.

While the invention has been particularly shown and described with reference to a preferred embodiment thereof, it will be understood by those skilled in the art that various changes in form and details may be made therein without departing from the spirit and scope of the invention.

The invention claimed is:

1. A sensor comprising:
a reference strip having a length, wherein the reference strip has thereon a first plurality of electrodes, wherein the reference strip is adapted to flexibly bend along its length, the reference strip having a first point along its length;
a sliding strip, wherein the sliding strip has thereon a second plurality of electrodes, wherein the sliding strip is operatively secured to the reference strip at the first point, wherein the sliding strip is configured to flexibly bend in response to bending of the reference strip; and
circuitry operably connected to the first plurality of electrodes and the second plurality of electrodes, the circuitry being adapted to take a plurality of measurements, each measurement corresponding to a distance between one of the first plurality of electrodes and one of the second plurality of electrodes, wherein the plurality of measurements are used to determine the shape of the reference strip along its length.

2. The sensor of claim 1, further comprising a spacer between the reference strip and the sliding strip.

3. The sensor of claim 1, wherein the first point is a distal end of the reference strip.

4. The sensor of claim 1, wherein the measurements from the first plurality of electrodes and the second plurality of electrodes correspond to arcs of the reference strip.

5. The sensor of claim 1, wherein the measurements from the first plurality of electrodes and the second plurality of electrodes are correspond to linear segments of the reference strip.

6. The sensor of claim 1, wherein the reference strip is one of a plurality of reference strips and the sliding strip is one of a plurality of sliding strips.

7. The sensor of claim 6, wherein the plurality of reference strips and the plurality of sliding strips form a mesh structure.

8. The sensor of claim 1, wherein the first plurality of electrodes are formed as complementary triangular electrodes.

9. A sensor comprising:
a reference strip having a length, the reference strip comprising a first and second electrode at a first and second position along the length, the reference strip being adapted to flexibly bend along its length;
a sliding strip comprising a first sliding strip electrode, wherein the sliding strip is configured to remain parallel to the reference strip and to flexibly bend in response to bending of the reference strip, and wherein the first sliding strip electrode is configured to be between the first and the second position along the length of the reference strip when the reference strip is flat; and, circuitry operably connected to the first electrode, the second electrode and the first sliding strip electrode, the circuitry being adapted to take measurements corresponding to:

a distance between the first electrode and the first sliding strip electrode, and a distance between the second electrode and the first sliding strip electrode; and, wherein the measurements are used to determine a bend of the reference strip along its length.

10. The sensor of claim 9, wherein the reference strip further comprises a third electrode at a third position along the length; wherein the sliding strip further comprises a second sliding strip electrode, wherein the second sliding strip electrode is configured to be between the second and the third position along the length of the reference strip when the reference strip is flat; and wherein the circuitry is operably connected to the first, second and third electrode, and the first and second sliding strip electrode, the circuitry being further adapted to take measurements corresponding to:

a distance between the second electrode and the second sliding strip electrode, and a distance between the third electrode and the second sliding strip electrode; and, wherein the measurements are used to determine the shape of the reference strip along its length.

11. The sensor of claim 10, wherein the first, second and third electrodes, and the first and second sliding strip electrodes are triangular electrodes.

12. The sensor of claim 9, further comprising a spacer between the reference strip and the sliding strip.

13. The sensor of claim 9, wherein the measurements taken correspond to arcs of the reference strip.

14. The sensor of claim 9, wherein the measurements taken correspond to linear segments of the reference strip.

15. A sensor comprising:

a reference strip having a length, the reference strip comprising a first and second electrode at a first and second position along the length, respectively, the reference strip being adapted to flexibly bend along its length;

a sliding strip comprising a first sliding strip electrode and a second sliding strip electrode, wherein the sliding strip is configured to remain parallel to the reference strip and to flexibly bend in response to bending of the reference strip, and wherein the first sliding strip electrode is configured to be between the first and the second position along the length of the reference strip when the reference strip is flat, and the second sliding strip electrode is configured not to be between the first and second position along the length of the reference strip when the reference strip is flat; and circuitry operably connected to the first and second electrode, and the first and second sliding strip electrode, the circuitry being adapted to take measurements corresponding to:

a distance between the first electrode and the first sliding strip electrode, and a distance between the second electrode and the second sliding strip electrode; and wherein the measurements are used to determine the shape of the reference strip along its length.

16. The sensor of claim 15, wherein the first and second electrodes, and the first and second sliding strip electrodes are triangular electrodes.

17. The sensor of claim 15, wherein the first and second electrodes, and the first and second sliding strip electrodes are rectangular electrodes.

18. The sensor of claim 15, further comprising a spacer between the reference strip and the sliding strip.

19. The sensor of claim 15, wherein the measurements taken correspond to arcs of the reference strip.

20. The sensor of claim 15, wherein the measurements taken correspond to linear segments of the reference strip.

* * * * *